US008907116B2

(12) United States Patent
Allais et al.

(10) Patent No.: US 8,907,116 B2
(45) Date of Patent: Dec. 9, 2014

(54) PROCESS FOR REMOVING AN ALKANOL IMPURITY FROM A DIALKYL CARBONATE STREAM

(75) Inventors: Cyrille Paul Allais, Amsterdam (NL); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 111 days.

(21) Appl. No.: 13/390,124

(22) PCT Filed: Aug. 10, 2010

(86) PCT No.: PCT/EP2010/061587
§ 371 (c)(1),
(2), (4) Date: May 4, 2012

(87) PCT Pub. No.: WO2011/018448
PCT Pub. Date: Feb. 17, 2011

(65) Prior Publication Data
US 2012/0226065 A1      Sep. 6, 2012

(30) Foreign Application Priority Data
Aug. 12, 2009    (EP) .................................... 09167737

(51) Int. Cl.
*C07C 68/06*    (2006.01)
*C07C 67/03*    (2006.01)
*C07C 68/08*    (2006.01)

(52) U.S. Cl.
CPC .................. *C07C 68/08* (2013.01); *C07C 67/03* (2013.01); *C07C 68/06* (2013.01)
USPC ........................................................ 558/260

(58) Field of Classification Search
None
See application file for complete search history.

(56) References Cited

U.S. PATENT DOCUMENTS

| 3,642,858 | A | 2/1972 | Freval et al. |
| 3,803,201 | A | 4/1974 | Gilpin et al. .................. 260/463 |
| 4,062,884 | A | 12/1977 | Romano et al. |
| 4,508,927 | A | 4/1985 | Bhise et al. |
| 4,691,041 | A | 9/1987 | Duranleau et al. |
| 5,292,917 | A | 3/1994 | Nishihira et al. ............. 558/277 |
| 5,359,118 | A | 10/1994 | Wagner et al. ................ 558/277 |
| 5,508,442 | A | 4/1996 | Wagner et al. |
| 2005/0010063 | A1 | 1/2005 | Murphy et al. |
| 2006/0194978 | A1 | 8/2006 | Murphy et al. |

FOREIGN PATENT DOCUMENTS

| CN | 1809624 | 7/2006 | |
| EP | 001082 | 6/1978 | ............. C07C 69/96 |
| EP | 180387 | 10/1985 | ........... C07D 301/02 |
| EP | 274953 | 7/1988 | ............... B01J 23/02 |
| EP | 0658536 | 6/1995 | ............. C07C 68/08 |
| EP | 1760059 | 3/2007 | |
| JP | 2002371037 | 12/2002 | ............. B01D 3/14 |
| JP | 2003300917 | 10/2003 | ............. B01D 3/38 |
| JP | 2006069997 | 3/2006 | ............. C07C 68/08 |
| WO | WO 2004/113264 | * 12/2004 | ............. C07C 68/00 |

OTHER PUBLICATIONS

Machine translation of JP 2003-300917, obtained from <http://worldwide.espacenet.com/>, Accessed Feb. 23, 2014.*
Knifton, J. F. et al., Ethylene Glycol-Dimethyl Carbonate Cogeneration, Journal of Molecular Catalysis, vol. 67 (1991) pp. 389-399.
Chinese Office Action issued Sep. 30, 2013 by State Intellectual Property Office for Ref. No. TS2392 CHNP, Chinese Patent Application No. 201080035736.2.

* cited by examiner

*Primary Examiner* — Alicia L Otton

(57) ABSTRACT

The invention relates to a process for removing an alkanol impurity from a stream containing a dialkyl carbonate and the alkanol impurity, comprising contacting the stream with an aryl group containing ester and a catalyst to effect reaction of the alkanol impurity with the aryl group containing ester.

17 Claims, No Drawings

PROCESS FOR REMOVING AN ALKANOL IMPURITY FROM A DIALKYL CARBONATE STREAM

PRIORITY CLAIM

The present application claims priority from PCT/EP2010/061587, filed 10 Aug. 2010, which claims priority from European application 09167737.7, filed 12 Aug. 2009.

The present invention relates to a process for removing an alkanol impurity from a stream containing a dialkyl carbonate and the alkanol impurity.

Dialkyl carbonates can be produced by reaction of alkylene carbonate with alkanol. Where alkylene carbonate (such as ethylene carbonate) is reacted with alkanol (such as ethanol), the products are dialkyl carbonate (such as diethyl carbonate) and alkanediol (such as monoethylene glycol). Such process is well-known and an example thereof is disclosed in U.S. Pat. No. 5,359,118. This document discloses a process in which di($C_1$-$C_4$ alkyl) carbonates and alkanediols are prepared by transesterification of an alkylene carbonate with a $C_1$-$C_4$ alkanol.

An example of an alkanol impurity that may be contained in a dialkyl carbonate stream is an ether alkanol, for example an alkoxy alkanol. JP2003300917 and JP2002371037 relate to processes wherein dimethyl carbonate and monoethylene glycol are made from ethylene carbonate and methanol and wherein 2-methoxyethanol is formed as a by-product. In the inventions of JP2003300917 and JP2002371037, said 2-methoxyethanol is removed by specific distillation techniques.

In a reactor where ethanol and ethylene carbonate are reacted into diethyl carbonate and monoethylene glycol, a side-reaction of ethanol with ethylene oxide, formed by back-reaction of ethylene carbonate into ethylene oxide and carbon dioxide, into 2-ethoxyethanol (ethyl oxitol) may take place. Further, ethyl oxitol may be formed by a side-reaction of ethanol with ethylene carbonate in such a way that carbon dioxide is released and ethyl oxitol is produced. Still further, a side-reaction between ethanol and monoethylene glycol may take place producing ethyl oxitol and water. Still even further, ethyl oxitol may be formed via decarboxylation of hydroxyethyl ethyl carbonate.

Therefore, the product stream from a reactor where ethanol and ethylene carbonate are reacted into diethyl carbonate and monoethylene glycol, may comprise unconverted ethanol, unconverted ethylene carbonate, diethyl carbonate, monoethylene glycol and the above-mentioned ethyl oxitol impurity. The presence of said alkoxy alkanol impurity may be detrimental in any subsequent production process. Said alkoxy alkanol impurity may for example end up in the dialkyl carbonate that is used as a starting material for the synthesis of diphenyl carbonate from said dialkyl carbonate and phenol. For example, in a case where the dialkyl carbonate is diethyl carbonate and the alkoxy alkanol impurity is ethyl oxitol, said ethyl oxitol may react with the phenol starting material and/or with the diphenyl carbonate product.

Direct reaction of phenol and ethyl oxitol may result in the production of phenyl 2-ethoxyethyl ether, and hence in the loss of valuable phenol reactant. Further, such reaction results in the introduction of undesired chemicals in the process and therefore to separation issues.

Reaction of diphenyl carbonate with ethyl oxitol results in product loss as phenyl 2-ethoxyethyl carbonate is produced. Further, the latter product acts as a "poison" in any subsequent polymerisation of diphenyl carbonate into polycarbonate material. For example, when diphenyl carbonate is reacted with bis-phenol A (BPA), polycarbonate and phenol are formed. Diphenyl carbonate can react with BPA since phenol is a relatively good leaving group. Dialkyl carbonates (such as diethyl carbonate) however cannot be used to produce polycarbonate by reaction with BPA, since alkanols are not good leaving groups. Alkoxy alkanols (such as ethyl oxitol) are neither good leaving groups. Therefore, in case phenyl 2-ethoxyethyl carbonate is present in a diphenyl carbonate feed to be reacted with BPA, phenol will be released easily from said phenyl 2-ethoxyethyl carbonate but not ethyl oxitol which will consequently stop the polymerization process at one end of the chain. Consequently, phenyl 2-ethoxyethyl carbonate has to be removed from diphenyl carbonate before the latter is contacted with BPA.

The above exemplifies that in a case where a dialkyl carbonate stream containing an alkanol impurity is formed, it is desired to remove said alkanol impurity before any subsequent process takes place wherein the dialkyl carbonate is transformed into a valuable end product. For example, it is needed to remove any ethyl oxitol impurity from a diethyl carbonate stream containing said impurity before reaction of the diethyl carbonate with phenol takes place.

Referring to the above example where ethanol and ethylene carbonate have been reacted into diethyl carbonate and monoethylene glycol, the product stream also containing unconverted ethanol and ethylene carbonate and ethyl oxitol side-product, may be separated by means of distillation. The boiling points for the various components in said product stream are mentioned in the table below.

| Component | Boiling point (° C.) |
|---|---|
| ethanol | 78.4 |
| diethyl carbonate | 126-128 |
| ethyl oxitol | 135 |
| monoethylene glycol | 197.3 |
| ethylene carbonate | 260.4 |

The distillation as referred to above may result in a top stream containing diethyl carbonate and unconverted ethanol and a bottom stream containing monoethylene glycol and unconverted ethylene carbonate. Most likely, all of the ethyl oxitol ends up in the top stream. However, depending on the specific conditions under which distillation is carried out, part of the ethyl oxitol may end up in the bottom stream. Subsequently, said top stream may be further separated by means of distillation into a top stream containing unconverted ethanol which can be recycled to the reactor where diethyl carbonate and monoethylene glycol are produced, and a bottom stream containing diethyl carbonate and the ethyl oxitol impurity.

As discussed above, before a dialkyl carbonate is transformed into a valuable end product in any subsequent process, the alkanol impurity has to be removed therefrom as that might interfere said subsequent process and/or any further processes. For the above example, this means that the ethyl oxitol impurity should be removed from the bottom stream containing diethyl carbonate and the ethyl oxitol impurity. In principle, ethyl oxitol and diethyl carbonate could be separated by means of a further distillation step. However because of the small difference in boiling point between diethyl carbonate and ethyl oxitol (see above table), such separation is very cumbersome requiring many distillation steps and stages. Therefore, there is a need to find a simple method of removing an alkanol impurity from a dialkyl carbonate stream containing such alkanol impurity.

Surprisingly it was found that by contacting the dialkyl carbonate stream with an aryl group containing ester and a catalyst, such alkanol impurity is removed from such stream by reaction of the alkanol impurity with the aryl group containing ester.

Accordingly, the present invention relates to a process for removing an alkanol impurity from a stream containing a dialkyl carbonate and the alkanol impurity, comprising contacting the stream with an aryl group containing ester and a catalyst to effect reaction of the alkanol impurity with the aryl group containing ester.

In the present invention, the alkanol impurity should be removed from the dialkyl carbonate stream before the dialkyl carbonate is used as a starting material in any subsequent process, for example before the dialkyl carbonate is reacted with phenol in the synthesis of diphenyl carbonate.

The aryl group containing ester contains one or more ester moieties of formula —(C=O)O—. A specific example of such ester moiety is a carbonate moiety of formula —O(C=O)O—. Further, the aryl group containing ester contains one or more aryl groups. The aryl group or at least one of the aryl groups may be attached directly to the non-carbonyl oxygen atom of an ester moiety of formula —(C=O)O— through one of the carbon atoms which constitute the aromatic ring of the aryl group.

Where the aryl group containing ester is a carbonate of formula $R_4O(CO)OR_5$, $R_4$ or $R_5$ is an aryl group, the other group being an alkyl group, or both $R_4$ and $R_5$ are aryl groups. Preferably, both $R_4$ and $R_5$ are aryl groups. Further, preferably, the aryl group is a phenyl group. The aryl group may be unsubstituted or substituted by an alkyl group, a heteroatom containing group such as a hydroxyl group, or a carbonyl group such as the carbonyl group from another ester moiety.

Examples of suitable aryl group containing carbonates for reaction with the alkanol impurity in the present process, are ethyl phenyl carbonate (EPC) and diphenyl carbonate (DPC). Preferably, the aryl group containing ester is DPC.

Where the aryl group containing ester is an ester of formula R'(CO)OR", R" is an aryl group, R' may be an alkyl group or an aryl group. Preferably, both R' and R" are aryl groups. The aryl group may be unsubstituted or substituted by an alkyl group, a heteroatom containing group such as a hydroxyl group, or a carbonyl group such as the carbonyl group from another ester moiety.

Preferably, R" is a phenyl group. Further, preferably, R' is a phenyl group substituted by a hydroxyl group at a position ortho with respect to the carbonyl group of the ester moiety. An example of such preferred aryl group containing ester for reaction with the alkanol impurity in the present process, is phenyl salicylate (phenyl 2-hydroxybenzoate).

Phenyl salicylate can be formed by internal rearrangement of DPC in a side-reaction during the production of DPC from a dialkyl carbonate and phenol and/or during purification of crude DPC.

Aryl group containing esters which are phenyl salicylate derivatives are also suitable for reaction with the alkanol impurity in the present process. Such phenyl salicylate derivatives are shown in the reaction scheme below:

Formula (I)

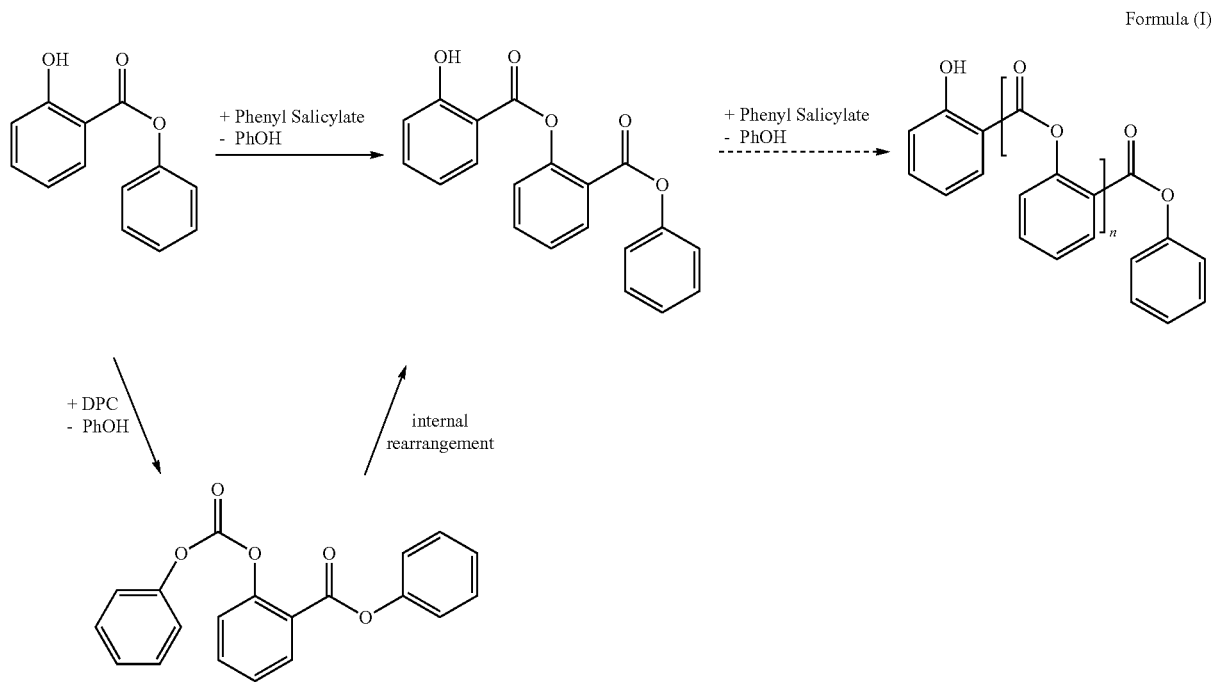

The phenyl salicylate derivatives shown in the above reaction scheme contain 2, 3 or more ester moieties of formulas —(C=O)O— and/or —O(C=O)O— and 1, 2 or more phenyl bridges between different ester moieties. These derivatives may have originated, directly or indirectly, from reaction of phenyl salicylate with itself, said phenyl salicylate being both an alcohol and an ester, or from reaction of phenyl salicylate with DPC, which reactions are shown in the above reaction scheme.

Other suitable phenyl salicylate derivatives are those wherein the hydroxyl group of phenyl salicylate is replaced by an alkoxide group —OR wherein R is an alkyl group, for example a methyl or an ethyl group.

The dialkyl carbonate in the stream from which the alkanol impurity has to be removed in accordance with the present invention, may be a di($C_1$-$C_5$)alkyl carbonate, wherein the alkyl groups (straight, branched and/or cyclic) may be the same or different, such as methyl, ethyl and propyl. Specifically, the dialkyl carbonate is diethyl carbonate.

The alkanol impurity which has to be removed from the stream containing the dialkyl carbonate and said impurity in accordance with the present invention, may be an ether alkanol, more specifically an alkoxy alkanol, most specifically 2-ethoxyethanol, as described above.

The amount of the alkanol impurity in the stream containing the dialkyl carbonate and said impurity may be comprised in the range of from 0.1 to 10 wt. %, specifically 0.3 to 8 wt. %, more specifically 0.5 to 6 wt. % and most specifically 0.5 to 5 wt. %.

The reaction of the alkanol impurity with the aryl group containing ester in the presence of a catalyst in accordance with the present invention, results in transesterification of the aryl group containing ester. Therefore, the catalyst that needs to be used in the process of the present invention should be a transesterification catalyst. Before the present invention is carried out, the stream containing a dialkyl carbonate and the alkanol impurity does not contain a catalyst. More in particular, said stream does not contain a transesterification catalyst before the present invention is carried out.

The transesterification catalyst to be added in the present invention may be one of many suitable homogeneous and heterogeneous transesterification catalysts known from prior art.

For example, suitable homogeneous transesterification catalysts have been described in U.S. Pat. No. 5,359,118 and include hydrides, oxides, hydroxides, alkanolates, amides, or salts of alkali metals, i.e., lithium, sodium, potassium, rubidium and cesium. Preferred homogeneous transesterification catalysts are hydroxides or alkanolates of potassium or sodium. Other suitable homogeneous transesterification catalysts are alkali metal salts, such as acetates, propionates, butyrates, or carbonates. Suitable catalysts are described in U.S. Pat. No. 5,359,118 and the references mentioned therein, such as EP274953A, U.S. Pat. No. 3,803,201, EP1082A, and EP180387A.

As mentioned above, it is also possible to employ a heterogeneous transesterification catalyst. Suitable heterogeneous catalysts include ion exchange resins that contain functional groups. Suitable functional groups include tertiary amine groups and quaternary ammonium groups, and also sulphonic acid and carboxylic acid groups. Further suitable catalysts include alkali metal and alkaline earth metal silicates. Suitable catalysts have been disclosed in U.S. Pat. No. 4,062,884 and U.S. Pat. No. 4,691,041. The heterogeneous catalyst may be selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff.

The heterogeneous transesterification catalyst to be used in the present invention may be a catalyst comprising an element from Group 4 (such as titanium; for example $TiO_2$ catalyst), Group 5 (such as vanadium), Group 6 (such as chromium or molybdenum) or Group 12 (such as zinc) of the Periodic Table of the Elements, or tin or lead, or a combination of such elements, such as a combination of zinc with chromium (for example zinc chromite). Said elements may be present in the catalyst as an oxide, such as zinc oxide. The transesterification catalyst to be used in the present invention may be a heterogeneous catalyst comprising zinc.

Specifically, the transesterification catalyst to be added in the present invention may be one of many suitable homogeneous and heterogeneous transesterification catalysts that are known to catalyze the formation of diphenyl carbonate from a dialkyl carbonate and phenol. More specifically, the transesterification catalyst is a titanium containing catalyst. Preferably, the titanium in said titanium containing catalyst has an oxidation state of IV. Further, said titanium may be bonded to one or more, preferably four, alkoxide groups, such as ethoxide groups, and/or aryloxide groups, such as phenoxide groups. An example of a suitable homogeneous transesterification catalyst is titanium(IV) 2-ethylhexyloxide (Ti$(OC_8H_{17})_4$).

Further, the above-mentioned titanium containing catalyst may be a dimer or polymer containing 2 or more titanium atoms, wherein titanium atoms may be bonded to each other via a carbonate bridge of formula —O(C=O)O— or via an oxygen bridge of formula —O—. Still further, said titanium containing catalyst may additionally contain one or more silicon atoms wherein the titanium and silicon atoms are bonded to each other via an oxygen bridge of formula —O—.

Preferably, the transesterification catalyst to be added in the present invention, such as the above-mentioned titanium containing catalyst, is present in a stream containing the aryl group containing ester that is to be reacted with the alkanol impurity in the present process. Advantageously, in that case, said transesterification catalyst and said aryl group containing ester do not have be added separately for reaction with the alkanol impurity in the present process.

Further, such stream containing both said transesterification catalyst, such as the above-mentioned titanium containing catalyst, and said aryl group containing ester, comprising for example DPC, may originate from a process for producing diphenyl carbonate from a dialkyl carbonate and phenol and/or purifying crude DPC, and may additionally contain heavy by-products. Even though part of such a stream can be recycled so that catalyst can be reused and DPC can be recovered, part of said stream has to be bled from the production process and disposed to prevent build-up of said heavy by-products.

In the present process, the stream containing the dialkyl carbonate and the alkanol impurity may advantageously be contacted with a stream (for example a bleed stream) originating from a process for producing diphenyl carbonate from a dialkyl carbonate and phenol and/or purifying crude diphenyl carbonate, the latter stream containing a catalyst, preferably a titanium containing transesterification catalyst such as those titanium containing catalysts as described above, and an aryl group containing ester, comprising preferably diphenyl carbonate and optionally one or more derivatives of diphenyl carbonate, comprising preferably phenyl salicylate and optionally one or more derivatives of phenyl salicylate, such as the phenyl salicylate derivatives as described above.

By combining said stream from a DPC production and/or purification process with the stream containing the dialkyl carbonate and the alkanol impurity in the present process, both said aryl group containing ester and said catalyst are effectively used to remove the alkanol impurity from the dialkyl carbonate, which is further explained below, rather than for example just being bled and disposed of. This leads to an improved efficiency of the overall, integrated process.

Further transesterification conditions are known in the art and suitably include a temperature from 40 to 200° C., and a pressure from 50 to 5000 kPa (0.5 to 50 bar).

In a case where the dialkyl carbonate is of formula $R_1OC(O)OR_2$ wherein $R_1$ and $R_2$ may the same or a different alkyl, the aryl group containing ester is a carbonate of formula $R_4O(CO)OR_5$ wherein $R_4$ or $R_5$ is an aryl group, the other group being an alkyl group, or both $R_4$ and $R_5$ are aryl groups, and the alkanol impurity is an alkanol of formula $R_3OH$ wherein $R_3$ may be an alkoxyalkyl group, the following reactions may take place when practising the present invention:

  (1)

  (2)

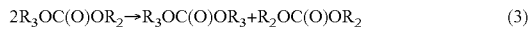  (3)

  (4)

  (5)

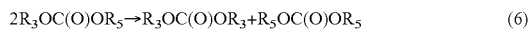  (6)

In a case where said $R_1OC(O)OR_2$ is diethyl carbonate (or EtOC(O)OEt), said $R_4OC(O)OR_5$ is diphenyl carbonate (or PhOC(O)OPh) and said $R_3OH$ is 2-ethoxyethanol (or EtOEtOH), the following reactions may take place in the presence of a transesterification catalyst:

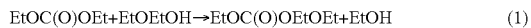  (1)

  (2)

(OxPC) is a mixed carbonate, namely phenyl 2-ethoxyethyl carbonate. EtOEtOC(O)OEtOEt (DOxC) is di(2-ethoxyethyl)carbonate.

Surprisingly, said alkanol impurity preferentially reacts with diphenyl carbonate rather than with diethyl carbonate. This advantageously results in a higher yield of diethyl carbonate as diethyl carbonate is saved which is a valuable starting material in the synthesis of diphenyl carbonate, and at the same time this results in the removal of the alkanol impurity which is converted into a compound that can be easily separated from diethyl carbonate by ordinary separation methods, which is further discussed below.

In addition, it has surprisingly been found that said alkanol impurity preferentially reacts with phenyl salicylate rather than with diethyl carbonate. This results in the same advantages as discussed above in connection with the preferential reaction with diphenyl carbonate.

In a case where said $R_1OC(O)OR_2$ is diethyl carbonate, the aryl group containing ester is the above-mentioned compound of formula (I), which is one of the above-mentioned derivatives of phenyl salicylate, and said $R_3OH$ is 2-ethoxyethanol, the following reactions (7) to (10) may take place in the presence of a transesterification catalyst:

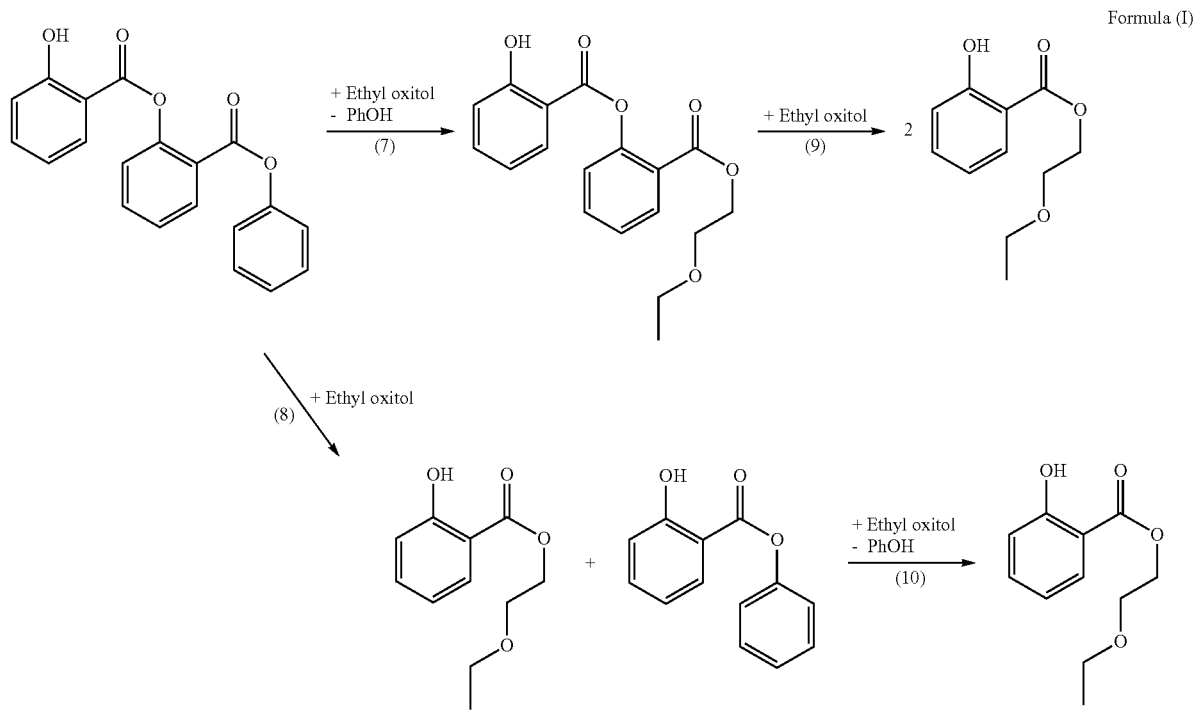

Formula (I)

  (3)

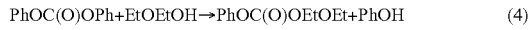  (4)

  (5)

  (6)

Said EtOC(O)OEtOEt (OxEC) is a mixed carbonate, namely ethyl 2-ethoxyethyl carbonate. Said PhOC(O)OEtOEt Reaction of said alkanol impurity with said aryl group containing ester of formula (I), rather than with diethyl carbonate, advantageously results in a higher yield of diethyl carbonate as diethyl carbonate is saved which is a valuable starting material in the synthesis of diphenyl carbonate, and at the same time this results in the removal of the alkanol impurity which is converted into a compound that can be easily separated from diethyl carbonate by ordinary separation methods, which is further discussed below.

In addition, the aryl group containing ester of formula (I) is a by-product in the production of diphenyl carbonate from a dialkyl carbonate and phenol, which by-product may thus be advantageously used in the present process to effectively remove another by-product, namely said alkanol impurity which may be formed in the production of a dialkyl carbonate from an alkylene carbonate and an alkanol. As a result, said aryl group containing ester of formula (I) advantageously does not have to be disposed of.

In a case where the stream containing the dialkyl carbonate and the alkanol impurity, is a stream containing a dialkyl carbonate that has been produced from reacting an alkanol with an alkylene carbonate, the stream usually contains unconverted alkanol reactant in addition to the alkanol impurity. Reference is made to the introduction of the present specification wherein the formation of such dialkyl carbonate stream is described.

In a case where the stream containing the dialkyl carbonate and the alkanol impurity, is a stream containing dialkyl carbonate, unconverted alkanol and an alkanol impurity, contacting of said stream with an aryl group containing ester and a transesterification catalyst to effect reaction of the alkanol impurity with the aryl group containing ester in accordance with the present invention, may be performed before, during or after the step wherein dialkyl carbonate is separated from unconverted alkanol.

Separation of the dialkyl carbonate from unconverted alkanol may be effected by means of distillation. Such distillation results in a top stream containing the unconverted alkanol (such as ethanol) and a bottom stream containing the dialkyl carbonate (such as diethyl carbonate), in a case where the unconverted alkanol has been reacted in a preceding step with an alkylene carbonate to produce the dialkyl carbonate and an alkanediol.

In a case where said contacting with an aryl group containing ester and transesterification catalyst is performed during said distillation step, the aryl group containing ester and the catalyst may be added to the distillation column itself or to a reactor of which the inlet and outlet are connected to said distillation column. The catalyst may be added together with the aryl group containing ester in one stream that contains both the catalyst and the aryl group containing ester, as described above.

Preferably, said contacting with an aryl group containing ester and transesterification catalyst is performed after said distillation step wherein the dialkyl carbonate is separated from unconverted alkanol. The bottom stream that originates from said (first) distillation step and which contains dialkyl carbonate but no longer unconverted alkanol, may be sent to a separate reactor or (directly) to a 2nd distillation column. In case it is sent to a separate reactor, the outlet stream of said reactor may be sent to a 2nd distillation column In said 2nd distillation column, purified dialkyl carbonate no longer containing the alkanol impurity is separated as a top stream. The aryl group containing ester and transesterification catalyst are added to the 2nd distillation column (or to said separate reactor, where applicable) either separately or in combination. Preferably, the catalyst is added together with the aryl group containing ester in one stream that contains both the catalyst and the aryl group containing ester, as described above. The bottom stream from said 2nd distillation column contains the catalyst and compounds having a higher boiling point than the dialkyl carbonate, as further illustrated below, and can be disposed of or further purified to recover any valuable component, such as catalyst and/or phenol. This is further explained below.

The present invention advantageously results in the removal of an alkanol impurity in dialkyl carbonate streams, which alkanol impurity might have interfered in any subsequent process using said dialkyl carbonate if it would not have been removed. It is recognised that by practising the present invention other impurities may be formed instead.

Where needed, said other impurities may easily be separated from the dialkyl carbonate to be purified by methods known to the skilled person, such as distillation, as described above. Therefore, the present process may further comprise the step of removing the impurities resulting from the reaction of the alkanol impurity with the aryl group containing ester, from the stream containing the dialkyl carbonate.

For example, in a case where a stream containing diethyl carbonate and 2-ethoxyethanol impurity has been contacted with a transesterification catalyst and DPC in accordance with the present invention, pure diethyl carbonate may easily be obtained by means of distillation in view of the boiling point differences between diethyl carbonate and the other compounds. This is indicated in the table below.

| Component | Boiling point (° C.) |
| --- | --- |
| diethyl carbonate | 126-128 |
| phenol | 182 |
| ethyl 2-ethoxyethyl carbonate | 190.2 (*) |
| di(2-ethoxyethyl) carbonate | 245.5 (*) |
| phenyl 2-ethoxyethyl carbonate | 281.2 (**) |
| diphenyl carbonate | 301 |

(*) Calculated using ACD/Labs Software V9.04 from Solaris ( ©1994-2008 ACD/Labs)
(**) Estimated using Emami, Valid, Elliot and Marrero, Gani group contribution methods (mean value).

Accordingly, the present invention also relates to a process for the preparation of a dialkyl carbonate and an alkanediol comprising:

(a) reacting an alkylene carbonate and an alkanol in the presence of a transesterification catalyst to obtain a product mixture containing unconverted alkylene carbonate, unconverted alkanol, dialkyl carbonate, alkanediol and an alkanol impurity;

(b) separating unconverted alkylene carbonate and alkanediol from the product mixture to obtain a top stream containing unconverted alkanol, dialkyl carbonate and the alkanol impurity;

(c) recovering the alkanediol; and (d) separating unconverted alkanol from the top stream containing unconverted alkanol, dialkyl carbonate and the alkanol impurity obtained in step (b) to obtain a bottom stream containing dialkyl carbonate and the alkanol impurity, which process further comprises (e) contacting the bottom stream containing dialkyl carbonate and the alkanol impurity obtained in step (d) with an aryl group containing ester and a catalyst to effect reaction of the alkanol impurity with the aryl group containing ester.

Accordingly, the present invention further also relates to a process for the preparation of a dialkyl carbonate and an alkanediol comprising:

(a) reacting an alkylene carbonate and an alkanol in the presence of a transesterification catalyst to obtain a product mixture containing unconverted alkylene carbonate, unconverted alkanol, dialkyl carbonate, alkanediol and an alkanol impurity;

(b) separating unconverted alkylene carbonate and alkanediol from the product mixture to obtain a top stream containing unconverted alkanol, dialkyl carbonate and the alkanol impurity;

(c) recovering the alkanediol; and (d) contacting the top stream containing unconverted alkanol, dialkyl carbonate and the alkanol impurity obtained in step (b) with an aryl group containing ester and a catalyst to effect reaction of the alkanol impurity with the aryl group containing ester, and separating unconverted alkanol to obtain a bottom stream containing dialkyl carbonate.

All of the above-described embodiments and preferences in relation to the above-described general process for removing an alkanol impurity from a stream containing a dialkyl carbonate and the alkanol impurity, comprising contacting the stream with an aryl group containing ester and a catalyst to effect reaction of the alkanol impurity with the aryl group containing ester, also apply to the two above-mentioned specific processes for the preparation of a dialkyl carbonate and an alkanediol, more in particular to step (e) and step (d), respectively, of said two processes.

In addition, the above-described transesterification catalyst and other transesterification conditions are equally applicable to steps (a) of said two processes for the preparation of a dialkyl carbonate and an alkanediol.

The present invention also relates to a process for the preparation of a dialkyl carbonate and an alkanediol comprising:
(i) reacting an alkylene carbonate and an alkanol in the presence of a transesterification catalyst in a distillation column, preferably a reactive distillation column, to obtain a top stream containing unconverted alkanol, dialkyl carbonate and an alkanol impurity and a bottom stream containing alkanediol and any unconverted alkylene carbonate;
(ii) recovering the alkanediol; and
(iii) separating unconverted alkanol from the top stream containing unconverted alkanol, dialkyl carbonate and the alkanol impurity obtained in step (i) to obtain a bottom stream containing dialkyl carbonate and the alkanol impurity,
which process further comprises
(iv) contacting the bottom stream containing dialkyl carbonate and the alkanol impurity obtained in step (iii) with an aryl group containing ester and a catalyst to effect reaction of the alkanol impurity with the aryl group containing ester.

The present invention further also relates to a process for the preparation of a dialkyl carbonate and an alkanediol comprising:
(i) reacting an alkylene carbonate and an alkanol in the presence of a transesterification catalyst in a distillation column, preferably a reactive distillation column, to obtain a top stream containing unconverted alkanol, dialkyl carbonate and an alkanol impurity and a bottom stream containing alkanediol and any unconverted alkylene carbonate;
(ii) recovering the alkanediol; and
(iii) contacting the top stream containing unconverted alkanol, dialkyl carbonate and the alkanol impurity obtained in step (i) with an aryl group containing ester and a catalyst to effect reaction of the alkanol impurity with the aryl group containing ester, and separating unconverted alkanol to obtain a bottom stream containing dialkyl carbonate.

All of the above-described embodiments and preferences in relation to the above-described general process for removing an alkanol impurity from a stream containing a dialkyl carbonate and the alkanol impurity, comprising contacting the stream with an aryl group containing ester and a catalyst to effect reaction of the alkanol impurity with the aryl group containing ester, also apply to the two above-mentioned specific processes for the preparation of a dialkyl carbonate and an alkanediol, more in particular to step (iv) and step (iii), respectively, of said two processes.

In addition, the above-described transesterification catalyst and other transesterification conditions are equally applicable to steps (i) of said two processes for the preparation of a dialkyl carbonate and an alkanediol.

Further, the present invention relates to a process for making a diaryl carbonate, comprising contacting a stream containing a dialkyl carbonate and an alkanol impurity with an aryl group containing ester and a catalyst to effect reaction of the alkanol impurity with the aryl group containing ester in accordance with any one of the above-described processes, and then contacting, in the presence of a transesterification catalyst, an aryl alcohol with the stream containing the dialkyl carbonate.

Preferably, said diaryl carbonate is diphenyl carbonate and said aryl alcohol is phenol.

In addition, the above-described transesterification catalyst and other transesterification conditions are equally applicable to said process for making a diaryl carbonate.

The invention is further illustrated by the following Examples.

REFERENCE EXAMPLE AND EXAMPLES 1-6

Transesterification experiments were performed by contacting diethyl carbonate (DEC) and 2-ethoxyethanol (ethyl oxitol) with either only catalyst (Reference Example) or with both catalyst and diphenyl carbonate (DPC; Examples 1 and 2) or phenyl salicylate (Example 3). The catalyst used was a commercially available heterogeneous catalyst comprising zinc, namely ZN-0312 T ⅛ (HT) catalyst supplied by BASF, which is a mixture of zinc oxide (about 65 wt. %) and zinc chromite ($Zn.Cr_2O_3$; about 35 wt. %). The reactions were performed in a 100 ml batch autoclave reactor equipped with a magnetic stirrer. To remove air and moisture, the filled reactor was purged three times with a stream of dry nitrogen before starting each of the experiments.

The experiments of Examples 4 and 5 were carried out in a similar way as Examples 1 and 2, with the proviso that the catalysts used were different. The catalysts used in Examples 4 and 5 were a heterogeneous titanium oxide ($TiO_2$ anatase) catalyst and a homogeneous titanium(IV) 2-ethylhexyloxide ($Ti(OC_8H_{17})_4$) catalyst, respectively.

The experiment of Example 6 was carried out in a similar way as Examples 1 and 2, with the proviso that a heavy carbonate fraction was used. Said heavy carbonate fraction was mainly comprised of DPC. Further, the heavy carbonate fraction contained other aryl group containing esters as contaminants, such as phenyl salicylate, 2-EPPC (2-ethylphenyl phenyl carbonate), 4-EPPC (4-ethylphenyl phenyl carbonate) and other unidentified heavy contaminants having a molecular weight greater than that of DPC (MW=214 g/mole) up to about 650 g/mole. Still further, the heavy carbonate fraction contained 0.4 mmole of titanium (Ti). The specific form of the titanium species as contained in the heavy carbonate fraction is unknown.

The titanium species as contained in said heavy carbonate fraction originated from the catalyst used in the preceding preparation of DPC from DEC and phenol. Said preparation involved reacting phenol and DEC in a first reactive distillation column in the presence of a titanium containing transesterification catalyst and separating by withdrawing a bottom stream containing DPC product (and its isomers), intermediate product ethyl phenyl carbonate, heavy impurities, a portion of unreacted phenol, a portion of unreacted DEC and traces of ethanol. In a second reactive distillation column, said bottom fraction was concentrated by removing phenol, DEC, ethanol and other light contaminants over the top of the column, and further reaction into DPC took place in said second column. The DPC containing bottom fraction from said second reactive distillation column was subjected to further distillation, wherein the main portion of the DPC was overheaded via the top stream from said column and the bottom stream therefrom contained the remaining DPC and isomers of DPC (such as phenyl salicylate) as well as heavy impurities (including 2-EPPC and 4-EPPC as mentioned above) and titanium species as mentioned above. The heavy carbonate fraction that was used in Example 6 was taken from the latter bottom stream.

2-ethoxyethyl carbonate (Examples 1, 2 and 4) or 2-ethoxyethyl salicylate (Example 3). The results for the Reference Example show that EEC is indeed formed in the absence of DPC and phenyl salicylate. Thus said Examples 1-4 show that even though DEC can react with ethyl oxitol, ethyl oxitol preferentially reacts with an aryl group containing ester, such as DPC or phenyl salicylate, rather than DEC.

| Examples | Ref. | 1 | 2 | 3 | 4 | 5 | 6 |
|---|---|---|---|---|---|---|---|
| Start conditions | | | | | | | |
| Diethyl carbonate (wt. %) | 88.2 | 42.7 | 58.7 | 31.6 | 60.1 | 66.7 | 66.1 |
| Diphenyl carbonate (wt. %) | 0 | 44.2 | 27.7 | 0 | 27.2 | 29.2 | 0 |
| Phenyl salicylate (wt. %) | 0 | 0 | 0 | 55.5 | 0 | 0 | 0 |
| Heavy carbonate fraction (wt. %) | 0 | 0 | 0 | 0 | 0 | 0 | 31.0 |
| Ethyl oxitol (wt. %) | 3.6 | 4.4 | 3.9 | 3.8 | 3.7 | 3.9 | 2.9 |
| Catalyst (wt. %) | 8.2 | 8.7 | 9.7 | 9.1 | 9.0 | 0.1 | (1) |
| Molar ratio —(C=O)OEt to —(C=O)OPh | n.a. | 1.8 | 3.8 | 2.1 | 4.0 | 4.1 | >3.9 |
| Reaction conditions | | | | | | | |
| Temperature (° C.) | 120 | 120 | 120 | 120 | 180 | 180 | 180 |
| Duration (hours) | 6 | 18 | 5.33 | 5.33 | 5 | 4.83 | 4 |
| Results | | | | | | | |
| Ethyl 2-ethoxyethyl carbonate (EEC) formed? | yes | no | no | yes$^a$ | yes$^b$ | yes | yes |
| Phenyl 2-ethoxyethyl carbonate formed? | n.a. | yes | yes | n.a. | yes | yes | yes |
| 2-Ethoxyethyl salicylate formed? | n.a. | n.a. | n.a. | yes | n.a. | n.a. | n.d. |
| Conversion of ethyl oxitol (%) | n.d. | 100 | 81 | n.d. | 100 | 100 | 100 |

(1) = 0.4 mmole Ti in heavy carbonate fraction; n.a. = not applicable; n.d. = not determined
$^a$EEC/(EEC + 2-ethoxyethyl salicylate), based on GC-MS area count = 0.01 (1%)
$^b$EEC/(EEC + phenyl 2-ethoxyethyl carbonate), based on GC-MS area count = 0.06 (6%)

The table below further lists the start and reaction conditions and results of the experiments of the Reference Example and Examples 1-6. Under "Results" in said table, it is mentioned whether or not certain ethyl oxitol reaction products were detected. Gas chromatography (GC) and/or gas chromatography-mass spectrometry (GC-MS) were/was used to detect ethyl 2-ethoxyethyl carbonate and phenyl 2-ethoxyethyl carbonate. GC-MS was used to detect 2-ethoxyethyl salicylate.

Regarding all Examples 1-6, it appears from the table that all ethyl oxitol in a DEC stream containing said ethyl oxitol as a contaminant, can be converted by contacting with a catalyst and with aryl group containing esters, such as DPC, phenyl salicylate and derivatives thereof. In all of the Examples, ethyl oxitol reacted with such aryl group containing esters, resulting in phenyl 2-ethoxyethyl carbonate (Examples 1, 2 and 4-6) and 2-ethoxyethyl salicylate (Example 3). The latter carbonates can be easily separated from DEC by means of distillation. In some cases (Examples 3-6), DEC also reacted with ethyl oxitol. This is not problematic as generally the amount of contaminants is only relatively small so that not much DEC would be lost. In these Examples, the amount of the ethyl oxitol contaminant was set at a value in the range of from 2.9 to 4.4 wt. %. Besides, the reaction of said ethyl oxitol with DEC results in a product (i.e. ethyl 2-ethoxyethyl carbonate (EEC)), that can also be easily separated from DEC by means of distillation. Thus this also results in the removal of the ethyl oxitol from DEC.

More in particular, regarding Examples 1-4, it appears from the table that despite the presence of a relatively large amount of DEC, no or only a relatively small amount of EEC was formed by reaction of DEC with ethyl oxitol, so that no or not much DEC was lost. For the only (Examples 1-2) or main (Examples 3-4) ethyl oxitol reaction product was phenyl

What is claimed is:

1. A process for removing an alkanol impurity from a stream containing a dialkyl carbonate and the alkanol impurity, comprising contacting the stream with an aryl group containing ester and a transesterification catalyst such that the alkanol impurity reacts with the aryl group containing ester, wherein the dialkyl carbonate is a di($C_1$-$C_5$)alkyl carbonate and the alkanol impurity is an ether alkanol.

2. A process according to claim 1, wherein the aryl group containing ester is diphenyl carbonate.

3. A process according to claim 2, wherein the dialkyl carbonate is a diethyl carbonate.

4. A process according to claim 1, wherein the alkanol impurity is an alkoxy alkanol.

5. A process according to claim 4, wherein the dialkyl carbonate is diethyl carbonate and the alkanol impurity is 2-ethoxyethanol.

6. A process according to claim 1, wherein the alkanol impurity is 2-ethoxyethanol.

7. A process according to claim 1, wherein the stream containing the dialkyl carbonate and the alkanol impurity is contacted with a stream originating from a process for producing diphenyl carbonate from a dialkyl carbonate and phenol and/or purifying crude diphenyl carbonate, the latter stream containing a catalyst, and an aryl group containing ester.

8. A process according to claim 7 wherein the transesterification catalyst is a titanium containing catalyst.

9. A process according to claim 7 wherein the aryl group containing ester is selected from the group consisting of diphenyl carbonate and derivatives of diphenyl carbonate.

10. A process according to claim 9 wherein the derivatives of diphenyl carbonate are selected from the group consisting of phenyl salicylate and derivatives of phenyl salicylate.

11. A process according to claim 1, wherein the stream containing a dialkyl carbonate and the alkanol impurity is obtained by a process for the preparation of a dialkyl carbonate and an alkanediol comprising:
(a) reacting an alkylene carbonate and an alkanol in the presence of a transesterification catalyst to obtain a product mixture containing unconverted alkylene carbonate, unconverted alkanol, dialkyl carbonate, alkanediol and an alkanol impurity;
(b) separating unconverted alkylene carbonate and alkanediol from the product mixture to obtain a top stream containing unconverted alkanol, dialkyl carbonate and the alkanol impurity;
(c) recovering the alkanediol; and
(d) separating unconverted alkanol from the top stream containing unconverted alkanol, dialkyl carbonate and the alkanol impurity obtained in step (b) to obtain a bottom stream containing dialkyl carbonate and the alkanol impurity,
which process further comprises
(e) contacting the bottom stream containing dialkyl carbonate and the alkanol impurity obtained in step (d) with an aryl group containing ester and a catalyst to effect reaction of the alkanol impurity with the aryl group containing ester.

12. A process according to claim 11, wherein the alkylene carbonate is ethylene carbonate, the unconverted alkanol is ethanol, the dialkyl carbonate is diethyl carbonate, the alkanediol is monoethylene glycol and the alkanol impurity is 2-ethoxyethanol.

13. A process according to claim 1, wherein the stream containing a dialkyl carbonate and the alkanol impurity is obtained by a process for the preparation of a dialkyl carbonate and an alkanediol comprising:
(a) reacting an alkylene carbonate and an alkanol in the presence of a transesterification catalyst to obtain a product mixture containing unconverted alkylene carbonate, unconverted alkanol, dialkyl carbonate, alkanediol and an alkanol impurity;
(b) separating unconverted alkylene carbonate and alkanediol from the product mixture to obtain a top stream containing unconverted alkanol, dialkyl carbonate and the alkanol impurity;
(c) recovering the alkanediol; and
(d) contacting the top stream containing unconverted alkanol, dialkyl carbonate and the alkanol impurity obtained in step (b) with an aryl group containing ester and a catalyst to effect reaction of the alkanol impurity with the aryl group containing ester, and separating unconverted alkanol to obtain a bottom stream containing dialkyl carbonate.

14. A process according to claim 13, wherein the alkylene carbonate is ethylene carbonate, the unconverted alkanol is ethanol, the dialkyl carbonate is diethyl carbonate, the alkanediol is monoethylene glycol and the alkanol impurity is 2-ethoxyethanol.

15. A process according to claim 1, further comprising the step of removing impurities resulting from the reaction of the alkanol impurity with the aryl group containing ester, from the stream containing the dialkyl carbonate.

16. A process for making a diaryl carbonate, comprising contacting a stream containing a dialkyl carbonate and an alkanol impurity with an aryl group containing ester and a catalyst to effect reaction of the alkanol impurity with the aryl group containing ester in accordance with the process of claim 1, and then contacting, in the presence of a transesterification catalyst, an aryl alcohol with the stream containing the dialkyl carbonate.

17. A process according to claim 16, wherein the diaryl carbonate is diphenyl carbonate and the aryl alcohol is phenol.

* * * * *